United States Patent [19]

Chesterfield et al.

[11] Patent Number: 5,366,756
[45] Date of Patent: Nov. 22, 1994

[54] METHOD FOR TREATING BIOABSORBABLE IMPLANT MATERIAL

[75] Inventors: Michael P. Chesterfield, Norwalk; Robert D. Torgerson, Branford, both of Conn.

[73] Assignee: United States Surgical Corporation, Norwalk, Conn.

[21] Appl. No.: 898,340

[22] Filed: Jun. 15, 1992

[51] Int. Cl.$^5$ ............................................. A61F 2/28
[52] U.S. Cl. ............................... 427/2.26; 623/16; 424/426; 525/937; 523/113
[58] Field of Search .............. 427/2; 424/426; 523/105, 113; 525/937; 604/891.1; 623/11, 16, 18

[56] References Cited

U.S. PATENT DOCUMENTS

| | | | |
|---|---|---|---|
| 3,739,773 | 6/1973 | Schmitt et al. | 128/92 BC |
| 3,984,914 | 10/1976 | Schwartz | 32/10 A |
| 4,043,344 | 8/1977 | Landi et al. | 128/335.5 |
| 4,047,533 | 9/1977 | Perciaccante et al. | 128/335.5 |
| 4,118,522 | 10/1978 | Stellmach | 427/3 |
| 4,186,448 | 2/1980 | Brekke | 3/1.9 |
| 4,256,785 | 3/1981 | Dannelly | 427/222 |
| 4,365,359 | 12/1982 | Raab | 3/1.912 |
| 4,429,691 | 2/1984 | Niwa et al. | 128/92 C |
| 4,459,317 | 7/1984 | Lambert | 427/2 |
| 4,473,670 | 9/1984 | Kessidis | 523/105 |
| 4,526,909 | 7/1985 | Urist | 523/115 |
| 4,535,485 | 8/1985 | Ashman et al. | 623/16 |
| 4,536,158 | 8/1985 | Bruins et al. | 433/201.1 |
| 4,547,327 | 10/1985 | Bruins et al. | 264/16 |
| 4,578,384 | 3/1986 | Hollinger | 514/8 |
| 4,589,873 | 5/1986 | Schwartz et al. | 604/265 |
| 4,653,497 | 3/1987 | Bezwada et al. | 525/937 |
| 4,666,437 | 5/1987 | Lambert | 604/265 |
| 4,670,287 | 6/1987 | Tsuji | 427/3 |
| 4,701,341 | 10/1987 | Appelgren | 427/3 |
| 4,705,694 | 11/1987 | Buttazzoni et al. | 427/2 |
| 4,728,570 | 3/1988 | Ashman et al. | 428/327 |
| 4,801,475 | 1/1989 | Halpern et al. | 427/338 |
| 4,813,876 | 3/1989 | Wang | 433/224 |
| 4,834,747 | 5/1989 | Gogolewski | 623/1 |
| 4,857,602 | 8/1989 | Casey et al. | 525/408 |
| 4,894,231 | 1/1990 | Moreau et al. | 424/426 |
| 4,921,497 | 5/1990 | Sule et al. | 623/6 |
| 5,007,939 | 4/1991 | Delcommune et al. | 623/66 |
| 5,019,400 | 5/1991 | Gombotz et al. | 424/497 |
| 5,037,445 | 8/1991 | Sander et al. | 623/66 |
| 5,080,665 | 1/1992 | Jarrett et al. | 609/219 |
| 5,143,662 | 9/1992 | Chesterfield et al. | 264/8 |

FOREIGN PATENT DOCUMENTS

| | | |
|---|---|---|
| 0089782 | 9/1983 | European Pat. Off. |
| 0221772 | 5/1987 | European Pat. Off. |
| 0241252 | 10/1987 | European Pat. Off. |
| 0398497 | 11/1990 | European Pat. Off. |
| 0488218 | 6/1992 | European Pat. Off. |
| 1593288 | 7/1981 | United Kingdom |
| WO9200342 | 1/1992 | WIPO |

*Primary Examiner*—Shrive Beck
*Assistant Examiner*—Erma Cameron

[57] ABSTRACT

A porous bioabsorbable surgical implant material is prepared by coating particles of bioabsorbable polymer with a tissue ingrowth promoter. Typical polymers include polymers of glycolide, lactide, caprolactone, trimethylene carbonate, dioxanone and physical and chemical combinations thereof. The tissue ingrowth promoter can include calcium hydroxide and/or a hydrophillic coating material. The hydrophillic coating material can be bioabsorbable or non-bioabsorbable. A typical non-bioabsorbable hydrophillic coating material is polyhydroxymethylmethacrylate (PHEMA). The bioabsorbable implant material may also contain a therapeutic agent. Typical therapeutic agents include an antimicrobial agent, dye, growth factor and combinations thereof. Typically, the particles are prepared by rotary atomization and coated by spraying.

12 Claims, 1 Drawing Sheet

METHOD FOR TREATING BIOABSORBABLE IMPLANT MATERIAL

BACKGROUND OF THE INVENTION

1. Field of the Invention

The present invention concerns a porous implant material for inducing the growth of bone or other hard tissue into the pores of the implant material, and relates also to a method for producing such material.

2. Background of the Related Art

In the healing arts there is often a need for an implant material to replace, repair, or reconstruct hard tissue in the body of a patient. For example, hard-tissue implant materials are used in medicine and veterinary medicine as a prosthetic bone material to repair injured or diseased bone. Hard tissue implant materials are also used in the construction of prosthetic joints and to fix prosthetic joints to bone. In dentistry, hard tissue implant materials are used in the construction of prosthetic teeth and tooth roots and to replace or augment the edentulous ridge.

U.S. Pat. Nos. 4,535,485 and 4,536,158 disclose certain implantable porous prostheses for use as bone or other hard tissue replacement which are comprised of polymeric materials. The prostheses of these references are composed generally of polymeric particles. The particles have an inner core comprised of a first biologically-compatible polymeric material such as polymethylmethacrylate and an outer coating comprised of a second biologically-compatible polymeric material which is hydrophilic, such as polymeric hydroxyethylmethacrylate. The particles may incorporate a ratio-opaque material to render the particle visible in an X-ray radiograph. The particles may be bonded together to form a unitary structure which can be implanted in the body. Alternatively, a mass of the particles may be implanted in the body in an unbonded, granular form. In either the bonded or the unbonded form, interstices between the implanted particles form pores into which tissue can grow. Thus, the bioabsorbable particles serve as a structural support and guiding matrix for encroaching bone deposits derived ultimately from adjacent fresh bone. The hydrophilic coating on the particles facilitates infusion of body fluids into the pores of the implant, which facilitates the ingrowth of tissue into the pores of the implant.

U.S. Pat. No. 4,728,570 discloses a calcium hydroxide treated polymeric implant material. The polymeric material disclosed therein is polymethylmethacrylate (PMMA) having a coating of polyhydroxyethylmethacrylate (PHEMA). Calcium hydroxide is distributed in the mass of polymeric particles to induce the growth of hard tissue.

SUMMARY OF THE INVENTION

A method is provided herein for preparing a porous bioabsorbable surgical implant material. More specifically, the method of the present invention is directed to coating of bioabsorbable particles or beads with tissue ingrowth promoter(s).

In one aspect of the present invention, particles of a bioabsorbable implant material, such as any of the commonly known bioabsorbable polymers, are coated with calcium hydroxide by placing the particles of implant material in a bed of calcium hydroxide powder in a container such as a flat pan, compacting the bed of calcium hydroxide, and heating the bed to a temperature sufficient to tackify the outer surface of the implant particles thereby causing at least some calcium hydroxide powder to adhere thereto. Compacting the bed of powder may be accomplished by placing the container in a flexible bag, applying a vacuum to the interior of the bag, and preferably thereafter sealing the bag. The bag with its contents can then be placed in an oven for heating.

In another aspect of the present invention, the bioabsorbable particles are coated with a hydrophilic material, which can optionally be bioabsorbable or non-bioabsorbable. The coating material is first dissolved in a suitable solvent, and the solution is then sprayed onto the particles of the implant material, after which the coated material is dried.

The aspects of the present invention are preferably combined. Thus, the bioabsorbable particles are first coated with calcium hydroxide and then coated with either the bioabsorbable or non-bioabsorbable hydrophilic coating material.

DETAILED DESCRIPTION OF PREFERRED EMBODIMENTS

Figure 1:
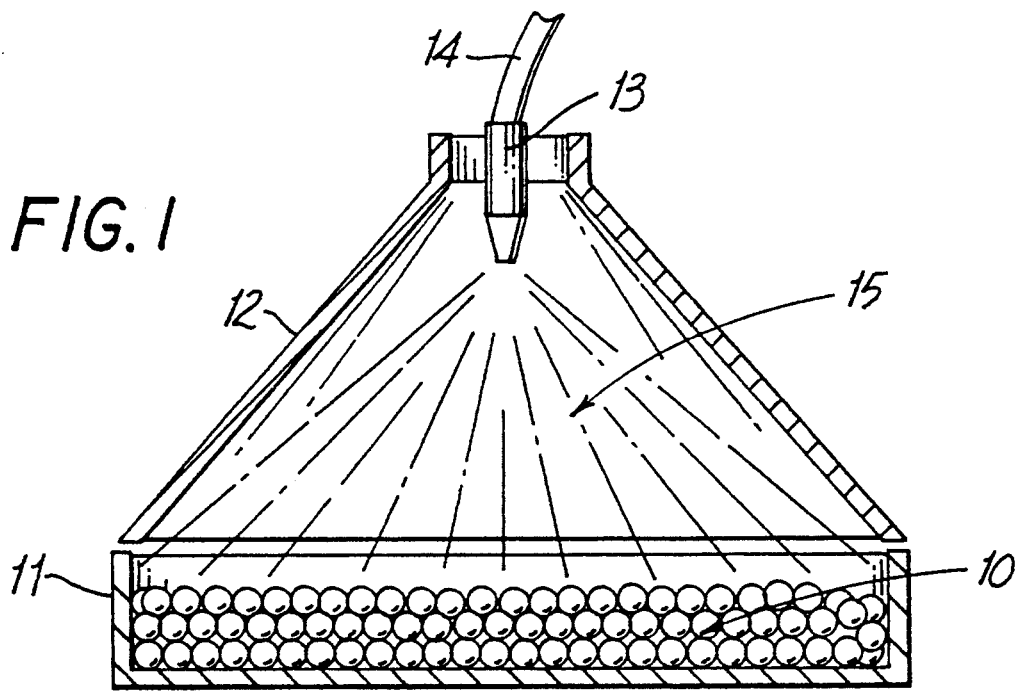
FIGS. 1 and 2 are diagrammatic views illustrating the spray coating method of the present invention in a non-fluidized bed and fluidized bed, respectively.

The present invention provides for the coating of bioabsorbable (i.e. resorbable) beads or particles for use as implantable packing material to replace, repair, or reconstruct hard tissue in the body of a patient. The particles employed in the present invention are preferably substantially spherical in shape and are prepared from a bioabsorbable material such as homopolymers and copolymers of, for example, glycolide, lactide, caprolactone, trimethylene carbonate, and dioxanone. Polymers of this type are known in the art, principally as materials for the fabrication of such surgical devices as sutures, wound clips, and the like, as disclosed, e.g., in U.S. Pat. Nos. 2,668,162; 2,703,316; 2,758,987, 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,060,089; 4,137,921; 4,157,437; 4,234,775; 4,237,920; 4,300,565; and, 4,523,591; U.K. Patent No. 779,291; D. K. Gliding et al, "Biodegradable polymers for use in surgery—polyglycolic/poly (lactic acid) homo- and co-polymers: 1", *Polymer*, Volume 20, pages 1459–1464 (1979) and D. F. Williams (ed.) *Biocompatibility of Clinical Implant Materials*, Vol. II, Ch. 9: "Biodegradable Polymers" (1981). Co-polymers of glycolide and lactide with or without additional monomers are preferred, and of these glycolide-lactide co-polymers are most preferred.

These particles can be prepared by a rotary atomization process, a description of which may be found in U.S. Pat. No. 5,143,662 filed Feb. 12, 1991 and herein incorporated by reference in its entirety. The particles can also be prepared by the methods disclosed in U.S. Pat. No. 5,102,783 and Ser. No. 618,652 filed on Apr. 2, 1990 and Nov. 27, 1990, respectively, both of which are herein incorporated by reference.

The particles of bioabsorbable implant material are coated with a tissue ingrowth promoter. When applied to the body as a porous mass of particles, the bioabsorbable implant material provides interstitial space for the body tissue to enter by ingrowth. Tissue ingrowth promoters render the interstitial space conducive to the ingrowth therein of body tissue by providing chemically and/or physically improved surface characteristics in the interior of the porous mass of particles. For example, a hydrophilic coating of the particles facilitates adequate penetration of the interstitial space with body fluids. A coating of calcium containing material stimulates the ingrowth of bone and/or hard tissue. Calcium hydroxide powder is preferred as a bone/hard tissue ingrowth promoter although other calcium containing compounds may be used such as hydroxyapatite.

In addition to materials for coating the finished biodegradable polymer particles, any desired drug, medicinal, or growth factor can be incorporated into the polymer itself prior to forming the particles, e.g., by addition to the polymer in the customary amounts so that at the conclusion of the polymeric particle manufacturing process, the particles will contain a predetermined amount of one or more of such substances which will be released gradually as the polymer is absorbed.

Thus, it is within the scope of this invention to incorporate one or more medico-surgically useful substances into the particles, e.g., those which accelerate or beneficially modify the healing process when particles are applied to a surgical repair site. For example, the bioabsorbable polymer particles can carry a therapeutic agent which will be deposited at the repair site. The therapeutic agent can be chosen for its antimicrobial properties, capability for promoting repair or reconstruction and/or new tissue growth or for specific indications such as thrombosis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a tissue repair site. A pharmaceutically acceptable dye can also be incorporated into the particles.

To promote repair and/or cell growth, one or several growth promoting factors can be introduced into the particles, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dismutase to scavenge tissue damaging free radicals, tumor necrosis factor for cancer therapy or colony stimulating factor and interferon, interleukin-2 or other lymphokine to enhance the immune system.

The particles are separated by size for different applications in reconstructive surgery in accordance with the following preferred procedure:

Size Sorting

One percent by weight calcium hydroxide powder, $Ca(OH)_2$, is added to a quantity of resorbable beads. Six eight inch diameter Standard Testing Sieves are stacked with a collection pan, on the bottom. The sieves are stacked in a vertical series of gradually smaller sorting sizes with the largest size sieve at the top and the smallest at the bottom just above the collection pan. The stack of sieves is placed in a mechanical sieve shaker.

A quantity of beads mixed with calcium hydroxide is placed in the top sieve tray, a lid is placed over the tray and the stack of sieve trays is agitated while a stream of nitrogen gas is purged upward through the stack from the bottom tray to maintain an inert atmosphere surrounding the beads. The beads are agitated for from 3 minutes to about an hour or more, until the beads have been sufficiently separated according to size. The beads that were collected on their respective sieves are poured into plastic bags.

After the beads have been sorted by size the appropriate size is selected and washed in accordance with the following preferred cleaning procedure. An appropriate range of sizes for surgical implant material is a particle diameter of from about 0.003 inches to about 0.08 inches.

Solvent Washing

The beads are washed with an appropriate solvent such as isopropanol. Other solvents such as methanol may also be used provided that the beads themselves are not dissolved by the solvent. A quantity of beads are placed in a container and isopropanol is added in the ratio of four parts isopropanol to one part beads. The mixture is agitated by stirring or by ultrasonic means for from 5 to 15 minutes. After agitation the solvent is decanted. The beads are preferably poured onto a sieve with a mesh size smaller than that of the beads. Isopropanol is then sprayed onto the beads to wash off any remaining unwanted residue.

The next step involves coating the beads with calcium hydroxide, which helps to stimulate bone and/or hard tissue ingrowth. The beads are mixed with calcium hydroxide and then heated to a temperature to make the bead surface sufficiently tacky to retain the calcium hydroxide particles. A preferred method of coating the beads is as follows:

Coating Procedure

The washed beads are placed in a pan with a thin bed of calcium hydroxide powder. The beads are spread out and a thin layer of additional calcium hydroxide is poured over the top of the layer of beads making sure that all of the beads are sufficiently coated. The pan containing the beads is then placed in a heat sealable flexible bag such as a polyethylene bag and a vacuum is then applied to the interior of the bag and the bag is sealed. Application of the vacuum causes the bag to compress the calcium hydroxide-bead mixture into a compact mass. The sealed bag is then placed in an oven and the entire apparatus is subjected to a temperature and duration sufficient to tackify the outer surface of the beads, i.e., for glycolide/lactide polymers, (a temperature of from about 60° C. to about 80° C. for from about 1 to about 3 hours). Upon completion of the heating cycle the bag is taken out of the oven and permitted to cool to ambient temperature. The pan is then removed from the bag and the beads are separated from the calcium hydroxide by means of a sieve. The beads are then spray washed with sterile water two to five times to remove excess calcium hydroxide. The beads are then vacuum dried for 24 hours or longer. When beads are fabricated from bioabsorbable materials which are not hydrophilic, it is highly desirable to coat the beads with a hydrophilic material to facilitate the permeation of body fluids into the implant to enable tissue ingrowth. Hydrophilic coatings facilitate tissue adhesion to the implant material and wetting of the implant by body fluids. Coatings are preferably from about 0.0001 inches to about 0.005 inches in thickness.

The hydrophilic coating material can be absorbable or non-absorbable. A preferred bioabsorbable hydrophilic coating comprises a blend of a glycolide/lactide copolymer and polyethylene oxide. A preferred non-bioabsorbable hydrophilic coating material comprises polyhydroxyethylmethacrylate (PHEMA).

Figure 2:
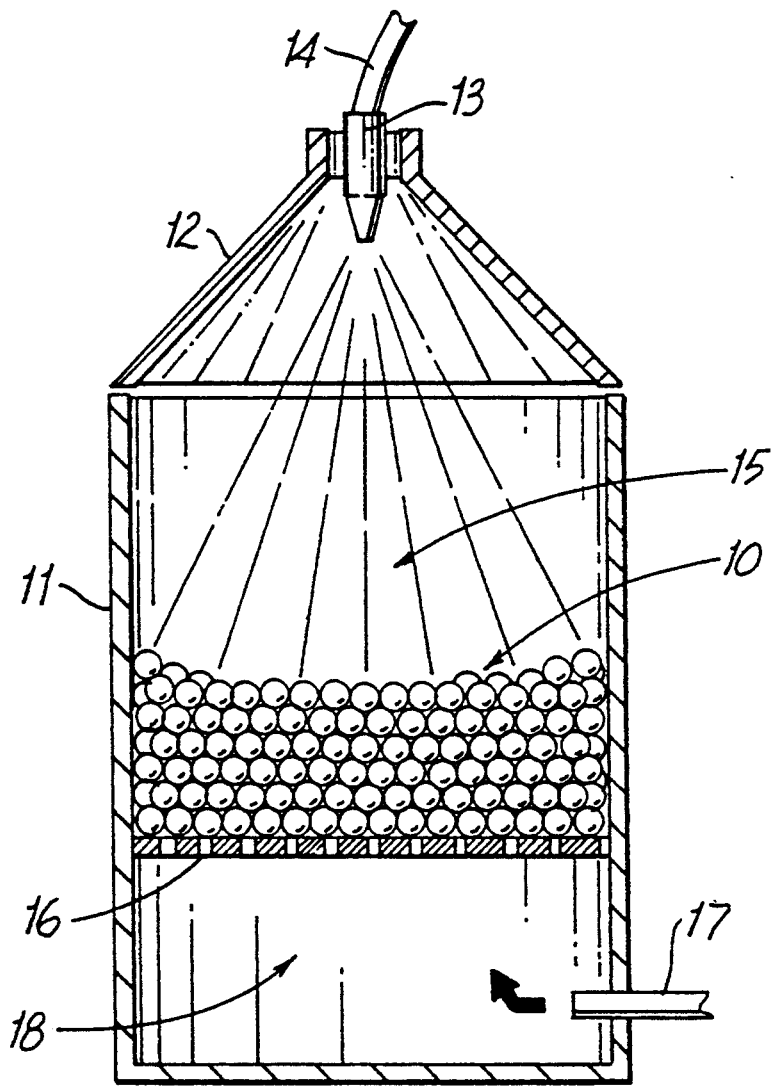

The hydrophilic coating can be applied by dissolving a prepolymerized coating material in a suitable solvent such as acetone, then spray coating the beads with the solution. Apparatus for spray coating the beads are illustrated in FIGS. 1 and 2. Alternatively the coating material may be applied to the beads by first applying a coating of the monomer and then polymerizing the monomer. For example, PHEMA coating can be applied to the beads by first coating the beads with a mixture of hydroxyethylmethacrylate monomer (HEMA) optionally mixed with from about 0.1% to about 5% by weight of a crosslinking agent such as a methacrylic diester of ethylene glycol, and then polymerizing the mixture to form a hydrophilic coating on the beads. Methacrylic diesters of ethylene glycol which are useful as crosslinking agents include tetraethylene glycol dimethacrylate, triethylene glycol dimethacrylate, diethylene glycol dimethacrylate, monoethylene glycol dimethacrylate, and mixtures thereof. Polymerization of the monomeric coating material may be accomplished by application of ionizing radiation, microwave radiation, or other suitable means.

Referring to FIG. 1, a layer of beads preferably from one to three beads thick is placed into container 11. A funnel shaped covering 12 is placed over the container to contain the spray. Nozzle 13 is fed by line 14 through which the coating solution flows. Nozzle 13 is positioned so as to direct spray 15 onto the beads 10. The container is preferably agitated while spraying to facilitate evenly applied coatings to the beads. The quantity by weight of coating material should be about 40% of the beads to be coated.

Referring to FIG. 2, an alternative embodiment of the spray apparatus employing a fluid bed operation may be used. Beads 10 are placed on a perforated plate 16 within container 11. A stream of gas such as air or, more preferably, nitrogen enters via inlet 17 into chamber 18 below the perforated plate 16. As the gas passes upward through the perforated plate and the beads, the bed of beads becomes fluidized. As with the previously described embodiment of FIG. 1, a covering 12 is employed to contain the spray 15 and nozzle 13 is positioned to direct spray 15 on the beads 10.

A further alternative to the fluid bed embodiment can include choosing a coating material of lower melting point than that of the beads and providing a bed containing a mixture of particles of coating material and beads. The bed is then fluidized and the temperature of the bed is raised to above that of the melting point of the particles of coating material but below that of the beads. The particles of coating material then melt and adhere to the beads. When the beads have been coated, the temperature of the bed is then gradually lowered to ambient after which fluidization may be halted. Heating may be accomplished by using a heated fluidizing gas.

After the beads have been coated, the container 11 with beads 10 is placed in an unheated chamber which is then evacuated to at least 30 millimeters of mercury to remove excess solvent.

The following example illustrates the method of the present invention wherein the following designations are employed:

Component A=a copolymer comprising 10% glycolide/90% lactide

Component B=a copolymer comprising 25% glycolide/75% lactide

Component C=a blend consisting of 50% of a copolymer of 18% glycolide/82% lactide, and 50% polyethylene oxide.

EXAMPLE 1

A quantity of Component A (6,000 grams) was heated to a temperature of 215° C. and applied at a rate of 50 g./min. from an extruder of the screw type to a rotary atomizer having a spinning disk of 76 cm. diameter and rotating at a rate of 180 rpm., with the disk being heated to a temperature of 250° C. This polymer, which was at a viscosity of 0.41 cp., was applied as a thin film of about 1.4 min. thick upon the spinning disk. The polymer film was broken up into particles which fell from the edge of spinning disk which was positioned at a height of 225 cm. above a collecting tray, so that the particles were sufficiently cooled to a temperature of 26° C. upon striking the tray.

The same procedure was repeated with a quantity of Component B at a viscosity of 0.39 cp., and with the rest of the numerical processing parameters maintained as described above. The resulting particles of bioabsorbable polymer were collected.

Particles of each component were added together to form a mixture of 50% by weight each of particles of Components A and B.

A quantity of the particle mixture was divided into three 5-gram samples, each sample being placed in a separate vial. The suitability of several liquids as washing fluids for the particles was tested by adding 10 ml of each solvent to a respective vial containing the beads. Water was added to sample 1, methanol was added to sample 2, and isopropanol was added to sample 3. Each sample was swirled for about 30 seconds then filtered under suction. An additional 5 ml of washing fluid was added to the beads in the filters. The samples were then dried overnight under a vacuum. The particles and washing fluids were then subjected to NMR testing.

The results show no significant dissolution of the particles in the washing fluids, which indicated that the aforementioned liquids are suitable for use in washing the particles after manufacture.

EXAMPLE 2

A sample of the mixed particles (20 mesh) of Example 1 were washed for 5 minutes with isopropanol (4 parts isopropanol to 1 part particles) and then suctioned and vacuum dried.

A quantity of calcium hydroxide ($Ca(OH)_2$) was placed on the bottom of a tray, 30 grams of the particles were poured into the tray over the ($Ca(OH)_2$), and more calcium hydroxide was added on top. The tray was then placed in a plastic bag. A vacuum pump was used to create a vacuum inside the bag, after which the bag was heat sealed. The sealed bag was then placed in an oven and heated to 60° C. for 1 hour. The particles were then removed and filtered using a size 30 mesh screen. The particles were then washed with stirring in a beaker with 10 parts sterile water to 1 part particles, after which the particles were vacuum dried.

EXAMPLE 3

A portion of the washed particles of Example 2 were coated with a hydrophilic absorbable coating material as follows:

Five grams of the particles were placed in a 1000 ml beaker. Two grams of Component C were dissolved in 6 grams of acetone. A funnel was inverted over the 1000 ml. beaker as diagrammed in FIG. 1 and an air brush was used to spray the Component C/acetone solution over the beads. The particles were then vacuum dried. Measurement of the weight of the particles after spraying and drying showed that about 0.42 grams of Component C, i.e. about 20%, remained on the particles.

EXAMPLE 4

A non-bioabsorbable coating material was prepared by providing a monomer mixture of HEMA with 2.5% by weight of triethylene glycol dimethacrylate (TEGDMA). Methods for preparing non-bioabsorbable coatings from HEMA are described in U.S. Pat. Nos. 4,728,570; 4,536,158 and 4,535,485, all of which are herein incorporated by reference.

Six vials were prepared, four vials (Vials 1 to 4 below) containing bioabsorbable beads prepared in accordance with the method of Examples 1 and 2, and two vials (Vials 5 and 6 below) containing, as a control, beads available from the Southwest Research Institute. The HEMA/TEGDMA monomer mixture was then added to the vials in accordance with the following proportions:

| Vial | Weight of Particles (grams) | Weight of Monomer (grams) |
| --- | --- | --- |
| 1 | 10.09 g | 0.51 g |
| 2 | 10.12 g | 1.01 g |
| 3 | 10.03 g | 1.51 g |
| 4 | 10.04 g | 1.51 g |
| 5 | 10.04 g | 0.50 g |
| 6 | 10.10 g | 1.53 g |

The vials were sealed and agitated, and then exposed to from about 2.4 Mrad to about 3.6 Mrad of gamma radiation from a cobalt-60 source, thereby polymerizing the HEMA to PHEMA.

What is claimed is:

1. A process for preparing surgical implant material comprising:
   a) providing a quantity of particles of bioabsorbable implant material; and
   b) coating said particles of bioabsorbable implant material with at least one tissue ingrowth promoter.

2. The process of claim 1, wherein said bioabsorbable implant material is a material selected from the group consisting of polymers of glycolide, lactide, caprolactone, trimethylene carbonate, dioxanone, and physical and chemical combinations thereof.

3. The process of claim 1, wherein said bioabsorbable implant material comprises a copolymer of glycolide and lactide.

4. The process of claim 1, wherein said bioabsorbable implant material contains a therapeutic agent selected from the group consisting of antimicrobial agent, dye, growth factor, and combinations thereof.

5. The process of claim 1, wherein said particles of bioabsorbable implant material are prepared by a rotary atomization process.

6. The process of claim 1, wherein said tissue ingrowth promoter comprises a hydrophilic material.

7. The process of claim 6, wherein said coating the particles of bioabsorbable implant material comprises providing a solution of a hydrophilic material in a solvent, spraying said particles with said solution, and evaporating the solvent from said particles thereby leaving a coating of hydrophilic material on the surfaces of said particles of bioabsorbable implant material.

8. The process of claim 6, wherein said coating the particles of bioabsorbable implant material comprises providing a monomeric hydrophilic coating material, coating said particles with said monomeric coating material, and then polymerizing said monomeric hydrophilic material to form a polymeric hydrophilic coating on said particles.

9. The process of claim 8, wherein said monomeric coating material includes hydroxyethylmethacrylate.

10. The process of claim 9, wherein said hydroxyethylmethacrylate is admixed with a crosslinking agent.

11. The process of claim 10, wherein said crosslinking agent is a methacrylic diester of ethylene glycol.

12. The process of claim 11, wherein said methacrylic diester of ethylene glycol is triethylene glycol dimethacrylate.

* * * * *